(12) United States Patent
Chuter

(10) Patent No.: US 6,293,969 B1
(45) Date of Patent: *Sep. 25, 2001

(54) BELL-BOTTOM MODULAR STENT-GRAFT

(75) Inventor: Timothy A. M. Chuter, Burlingame, CA (US)

(73) Assignee: Endovascular Technologies, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/469,341

(22) Filed: Dec. 20, 1999

Related U.S. Application Data

(63) Continuation of application No. 09/014,945, filed on Jan. 28, 1998, now Pat. No. 6,030,415.
(60) Provisional application No. 60/036,518, filed on Jan. 29, 1997.

(51) Int. Cl.[7] ........................................ A61F 2/06
(52) U.S. Cl. ........................................ 623/1.16; 623/1.35
(58) Field of Search .................... 623/1.1, 1.12, 623/1.13, 1.15, 1.16, 1.27, 1.28, 1.35, 1.36; 606/194, 195; 600/36

(56) References Cited

U.S. PATENT DOCUMENTS

| | | |
|---|---|---|
| 3,657,744 | 4/1972 | Ersek . |
| 4,562,596 | 1/1986 | Kornberg . |
| 4,994,071 | 2/1991 | MacGregor . |
| 5,316,023 | 5/1994 | Palmaz . |
| 5,360,443 | 11/1994 | Barone . |
| 5,489,295 | 2/1996 | Piplani . |
| 5,507,769 | 4/1996 | Marin . |
| 5,522,880 | 6/1996 | Barone . |
| 5,562,724 | 10/1996 | Vorwerk . |
| 5,562,726 | 10/1996 | Chuter . |
| 5,571,170 | 11/1996 | Palmaz . |
| 5,571,171 | 11/1996 | Barone . |
| 5,571,173 | 11/1996 | Parodi . |
| 5,575,817 | * 11/1996 | Martin ........................ 623/1 |
| 5,578,071 | 11/1996 | Parodi . |
| 5,578,072 | 11/1996 | Barone . |
| 5,591,228 | 1/1997 | Edoga . |
| 5,591,229 | 1/1997 | Parodi . |
| 5,609,625 | 3/1997 | Piplani . |
| 5,609,627 | 3/1997 | Goicoechea et al. . |
| 5,617,878 | 4/1997 | Taheri . |
| 5,628,781 | 5/1997 | Williams . |

(List continued on next page.)

FOREIGN PATENT DOCUMENTS

| | | |
|---|---|---|
| 0 646 365 A1 | 4/1995 | (EP) . |
| WO 8806026 | 8/1988 | (WO) . |
| WO 95/09586 | 4/1995 | (WO) . |
| WO 95/16406 | 6/1995 | (WO) . |
| WO 95/21592 | 8/1995 | (WO) . |
| WO 95/34255 | 12/1995 | (WO) . |
| WO 96/23455 | 8/1996 | (WO) . |
| WO 96/29955 | 10/1996 | (WO) . |
| WO 97/03717 | 2/1997 | (WO) . |
| WO 97/12562 | 4/1997 | (WO) . |
| WO 97/33532 | 9/1997 | (WO) . |

*Primary Examiner*—Dinh X. Nguyen
(74) *Attorney, Agent, or Firm*—Fulwider Patton Lee & Utecht, LLP

(57) ABSTRACT

A system for repairing body lumens including a modular graft and a method for deploying the graft within the body lumen. The modular graft includes a first component having first and second leg portions which mate with second and third graft components, respectively. The second leg portion has a bell bottom shape. The modular graft further includes expandable members which aid in implanting the modular graft as well as facilitates the mating of its components. In order to repair the body lumen, the first component is placed at the repair site and thereafter, the first and second legs are advanced to the repair site and attached to the first component.

11 Claims, 5 Drawing Sheets

U.S. PATENT DOCUMENTS

| | | |
|---|---|---|
| 5,628,783 | 5/1997 | Quiachon . |
| 5,632,763 | 5/1997 | Clastra . |
| 5,632,772 | 5/1997 | Alcime . |
| 5,639,278 | 6/1997 | Dereume et al. . |
| 5,643,208 | 7/1997 | Parodi . |
| 5,653,743 | 8/1997 | Martin . |
| 5,676,696 | 10/1997 | Marcade . |
| 5,676,697 | 10/1997 | McDonald . |
| 5,683,449 * | 11/1997 | Marcade ................................. 623/1 |
| 5,683,450 | 11/1997 | Goicoechea et al. . |
| 5,683,451 | 11/1997 | Lenker . |
| 5,683,452 | 11/1997 | Palmaz . |
| 5,683,453 | 11/1997 | Palmaz . |
| 5,693,086 | 12/1997 | Goicoechea et al. . |
| 5,693,087 | 12/1997 | Parodi . |
| 5,695,517 | 12/1997 | Marin et al. . |
| 5,709,713 | 1/1998 | Evans et al. . |
| 5,713,917 | 2/1998 | Leonhardt et al. . |
| 5,716,365 | 2/1998 | Goicoechea et al. . |
| 5,718,724 | 2/1998 | Goicoechea et al. . |
| 5,720,776 | 2/1998 | Chuter . |
| 5,755,772 | 5/1998 | Evans et al. . |
| 5,755,773 * | 5/1998 | Evans et al. ............................. 623/1 |
| 5,769,882 | 6/1998 | Fogarty et al. . |
| 5,769,885 | 6/1998 | Quiachon . |
| 5,776,180 * | 7/1998 | Goicoechea et al. .................... 623/1 |
| 5,800,508 | 9/1998 | Goicoechea et al. . |
| 5,824,036 | 10/1998 | Lauterjung . |
| 5,824,040 | 10/1998 | Cox et al. . |
| 5,843,158 | 12/1998 | Lenker et al. . |
| 5,843,160 | 12/1998 | Rhodes . |
| 5,855,598 | 1/1999 | Pinchuk . |

\* cited by examiner

IPSILATERAL FEMORAL ARTERY

CONTRALATERAL FEMORAL ARTERY

BELL-BOTTOM MODULAR STENT-GRAFT

This application is a continuation of application Ser. No. 09/014,945 filed Jan. 28, 1998, now U.S. Pat. No. 6,030,415 and also claims benefit of Provisional No. 60/036,518 filed Jan. 29, 1997.

FIELD OF THE INVENTION

The present invention is directed to an intraarterial prosthesis, a modular stent-graft, for repair of abdominal aortic aneurysm ("AAA" herein).

BACKGROUND OF THE INVENTION

An intraarterial prosthesis for the repair of AAAs (grafts) is introduced into the AAA through the distal arterial tree in catheter-based delivery systems, and is attached to the non-dilated arteries proximal and distal to the AAA by an expandable framework (stents). An intraarterial prosthesis of this type has two components: a flexible conduit, the graft, and the expandable framework, the stent (or stents). Such intraarterial prosthesis used to repair AAAs is named stent-graft. AAAs typically extend to the aortic bifurcation of the ipsilateral femoral artery and the contralateral femoral artery. There is rarely any non-dilated aorta below the aneurysm, and thus the distal end of the graft must be implanted in the iliac arteries, and for the graft to maintain prograde in-line flow to the legs and arteries of the pelvis, it must also bifurcate. Currently available stent-grants fall into two categories. The first category of stent-grafts are those in which a preformed bifurcated graft is inserted whole into the arterial system and manipulated into position about the AAA. This is a unitary stent-graft. The second category of stent-grafts are those in which a bifurcated graft is assembled in situ from two or more stent-graft components. This latter stent-graft is referred to as a modular stent-graft.

SUMMARY OF THE INVENTION

The present invention is directed to a modular stent-graft comprising multi-components. The modular stent-graft of the present invention eliminates or avoids the main drawbacks common to the currently available modular stent-grafts for repair of AAAs. Stent-grafts are inserted into the AAA through the femoral arterial system. The graft must bridge the AAA and form a leak-proof conduit between the aorta and the femoral arteries. The surgeon can only view the operation by X-ray techniques and yet the surgery is performed in a three-dimensional environment. This is a demanding regime and requires a trained and skilled surgeon.

The main drawbacks common to the current modular stent-grafts are:

(1) The connection site between the stent-graft components is prone to leakage and a separation of the components which allows blood to leak directly into the AAA restoring the potential for rupture. If the AAA ruptures, the result is frequently the death of the patient.

(2) The connection site on the first stent-graft component is often difficult to catheterize prior to introduction of the second stent-graft component. The necessary instrumentation required to insert catheters and carry out the repair of the abdominal aneurysm can dislodge mural thrombus in the AAA. The dislodged mural thrombus is carried in the blood flow through the femoral arteries to small distal arteries causing blockage and tissue necrosis.

The modular stent-graft of the present invention consists of three stent-graft components. The first stent-graft component resembles a pair of shorts with the trunk proximal and the two legs or docking sites distal. The second and third stent-graft components are tubes of almost uniform diameter that extend from the primary stent-graft component docking sites, through the AAA, to the femoral arteries. The completed modular stent graft bridges the AAA from the abdominal aorta to the femoral arteries. The proximal ends of the second and third stent-graft components, i.e., ends nearest the aorta, are inserted into the docking sites of the primary stent-graft. The second stent-graft component is inserted through the ipsilateral arteries to the ipsilateral docking site of the primary stent-graft component. The second stent-graft is also referred to as the ipsilateral extension. The third stent-graft component is inserted through the contralateral arteries to the contralateral docking site through the bell-bottom portion of the primary stent-graft component. The third stent-graft is also referred to as the contralateral extension.

The modular stent-graft of the present invention has a number of distinguishing elements. The stents that hold the two docking sites open are at different levels and are of different sizes. On the ipsilateral docking site, the stent is within the docking site. With regard to the contralateral docking site, the stent is within a wider distal segment, the bell-bottom segment below the contralateral docking site.

Because the distal stents of the primary stent-graft component are at different levels, one below the other, they occupy different segments of the delivery system. Since the stent-graft components are delivered to the AAA though a narrow catheter, they must be reduced to the smallest possible diameter to effect and ease delivery. By separating the stent-graft into three components, the necessary stents can be arranged at different levels permitting them to be as large as possible. Since the distal stents can be larger in a modular system than in a unitary system, the distal orifice of the ipsilateral and contralateral docking site can be large and thus easier to catheterize for the delivery. This is only important on the contralateral side, that is, the side with the contralateral docking site. On the ipsilateral side, that is, the side with the ipsilateral docking site, catheters can be introduced over the same guide wire that was used to introduce the first stent-graft component through the arterial system to the AAA. In practice, the distal orifice of the contralateral docking site can be at least as large as the trunk of the primary stent-graft component. The first stent-graft component 12 and the second and third stent-graft components 14 and 16 can be made of the same different biologically inert graft and stent material, such as biologically inert knit or woven fabric, or membrane material, such as PTFE membrane material, and springy material, such as stainless steel or titanium.

DETAILED DESCRIPTION OF THE INVENTION

Figure 1:
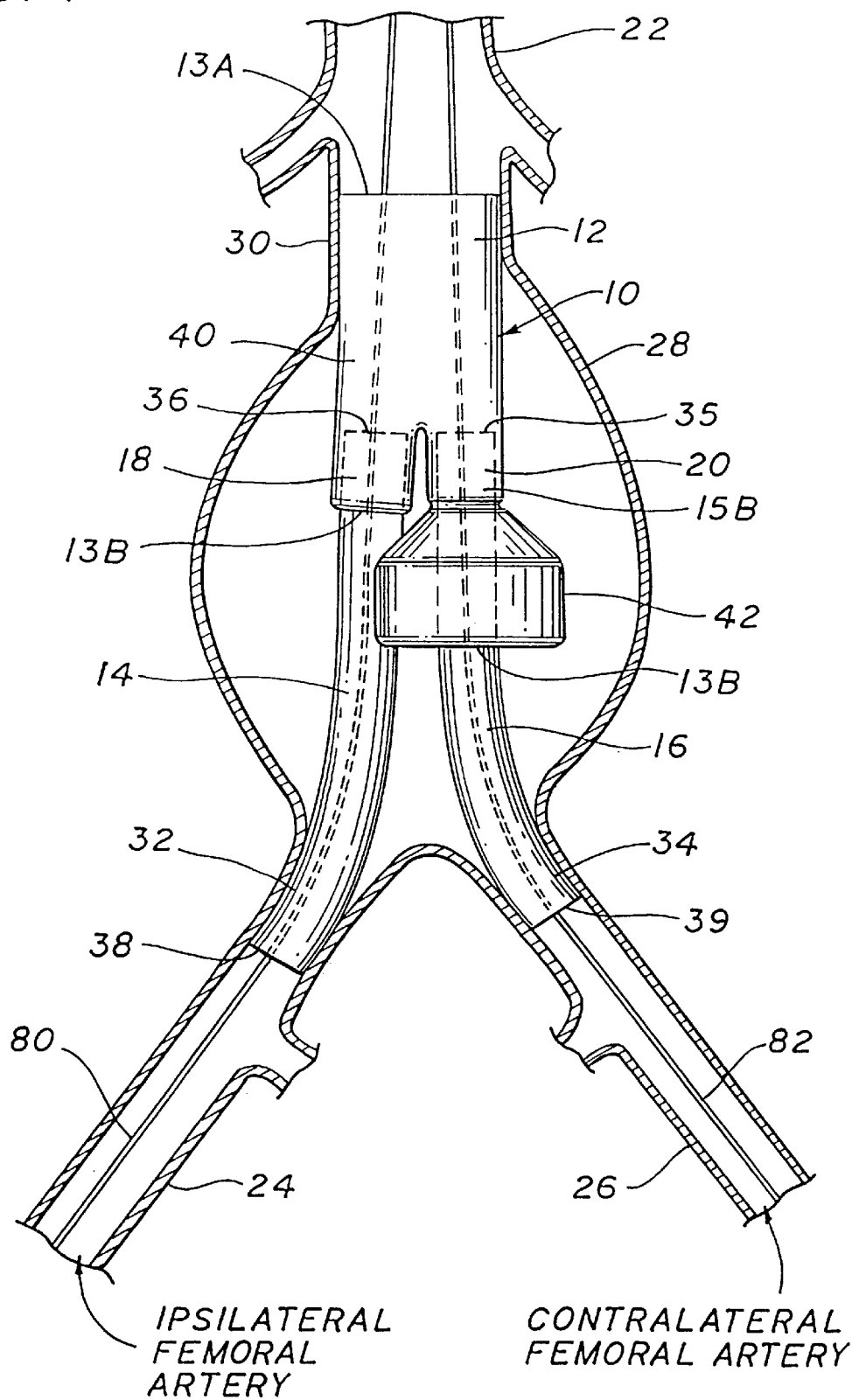
FIG. 1 is a cross-sectional view of the modular stent-graft of the present invention implanted to repair an abdominal aortic aneurysm.

Referring to FIG. 1, the modular stent-graft 10 of the present invention is illustrated implanted to repair an abdominal aorta aneurysm 28. The modular stent-graft 10 comprises a first stent-graft component 12 having a proximal end 13A and a distal end 13B, second stent-graft component 14, often referred to as the ipsilateral extension, and a third stent-graft component 16, often referred to as the contralateral extension. The three components comprise sheaths or grafts 41, 21 and 23 containing self-expanding stents (not shown in FIG. 1). The proximal end 13A of the trunk 40 of the first stent-graft component 12 is implanted in the proximal implantation site 30 in a non-dilated portion of the abdominal aorta 22. The proximal end 36 of the second stent-graft component, or ipsilateral extension, is connected to the first stent-graft component at the ipsilateral docking site 18. The proximal end 37 of the third stent-graft component 16, or contralateral extension, is connected to the first stent-graft component at the contralateral docking site 20. The distal end 38 of the second stent-graft component is implanted in the undilated portion of the ipsilateral iliac artery 24 at the ipsilateral distal implantation site 32. The distal end of the third stent-graft component, or contralateral extension, is implanted in a non-dilated portion of the contralateral iliac artery 26 at contralateral distal implantation site 34, as will be described herein. The contralateral leg 15B of the first stent-graft component terminates in a bell-bottom 42. Bell-bottom aids in the surgical implantation and manipulation of the modular stent-graft in the aorta and the aneurysm 28 as will be described below.

The ipsilateral catheter guide wire 80 is shown coming up from the ipsilateral arteries (the isilatoral femoral artery and ipsilateral iliac artery) into the ipsilateral extension through the ipsilateral docking site and out through the proximal end 13A of the trunk 40. The contralateral catheter guide wire 82 is shown extending up from the contralateral femoral artery through the contralateral iliac artery and through the contralateral extension 16 through the contralateral docking site 20 and out through the proximal end 13A of the trunk 40. Normally, both guide wires are left in until the completion of the operation. After the modular stent-graft has been successfully implanted to repair the abdominal aortic aneurysm, the guide wires are removed. In the preferred embodiment, the ipsilateral catheter guide wire 80 is first inserted to permit the delivery of the first stent-graft component and the ipsilateral extension into the AAA. The contralateral catheter guide wire 82 is inserted from the contralateral iliac artery 26 into the contralateral docking site 20 of the first stent-graft component. As mentioned above, the surgeon is viewing the three-dimensional environment of the AAA with a two-dimensional X-ray screen. The large bell-bottom 42 of the first stent-graft component eases the surgeon's task in successfully snaking the guide wire 82 up into the bell-bottom 42 and into the contralateral docking site 20. Obviously when the first guide wire 80 is inserted, the surgeon is concerned with having the guide wire come out of the ipsilateral iliac artery 24 through the AAA into the abdominal aorta 22. Without the bell-bottom 42 below the contralateral docking site 20, it would be very difficult, and in many instances impossible, to successfully snake the contralateral catheter guide wire 82 into the contralateral docking site 20 of the first stent-graft component.

Figure 2:
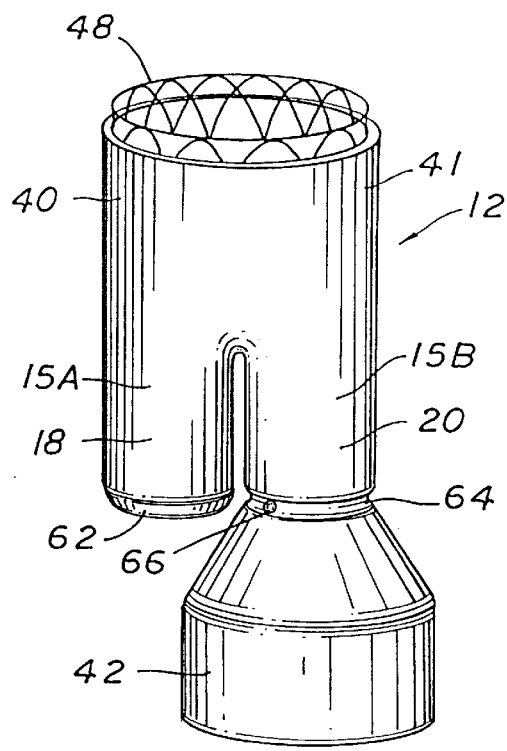
FIG. 2 is a front perspective view of the first stent-graft component of the modular stent-graft of FIG. 1.
Figure 3:
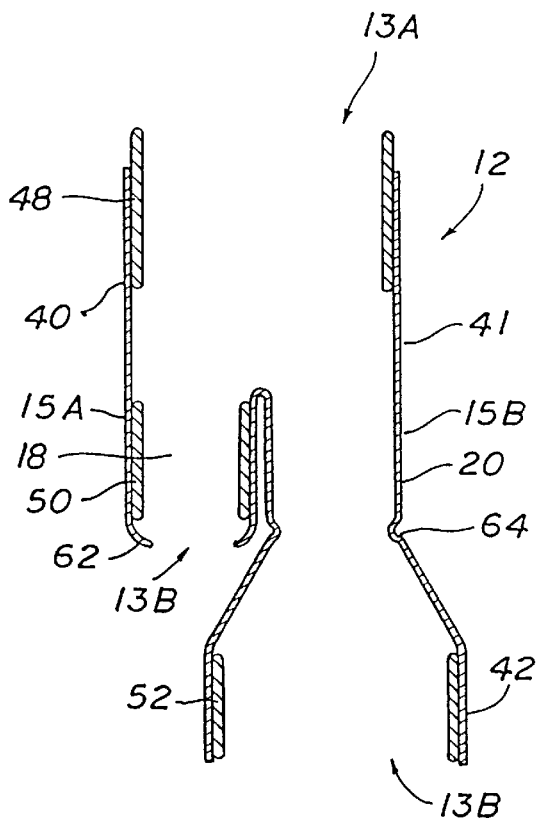
FIG. 3 is a cross-sectional view of the first stent-graft component of FIG. 2.

Referring to FIGS. 2 and 3, the first stent-graft component 12 of the modular stent-graft 10 comprises a trunk 40 at the proximal end 13A of the first stent-graft component and ipsilateral leg 15A and contralateral leg 15B at the distal end 13B of the first stent-graft component. The distal end of the ipsilateral leg 15A has a constricted portion 62. The contralateral leg 15B has a constricted portion 64 at approximately the same level as constricted portion 62. A radioopaque marker 66 is placed on the first stent-graft component in the constricted portion 64 adjacent the constricted portion 62, as shown in FIG. 2. This marker aids the surgeon in positioning the proximal stents of the ipsilateral and contralateral extensions. The first stent-graft component is delivered into the aorta aneurysm 28 via a conventional stent-graft catheter delivery system, such as disclosed in U.S. Pat. Nos. 4,580,568; 4,655,771; 4,830,003; 5,104,404; and 5,222,971. The modular stent-graft has three self-expanding stents: a proximal trunk stent 48, situated within the first stent-graft component at the proximal end 13A; an ipsilateral trunk stent 50, positioned within the first stent-graft component near the distal end 13B of the ipsilateral leg 15A; and a bell-bottom stent, located within the bell-bottom 42 at the distal end 13D of the contralateral leg 15D. These are self-expanding stents of the conventional type, such as disclosed in U.S. Pat. Nos. 4,580,568; 4,655,771; 4,830,003; 5,104,404; and 5,222,971. My self-expanding stent disclosed in U.S. patent application Ser. No. 08/582,943 can be used.

The stents employed in the present invention are self-expanding and thus are constricted in the catheter delivery system. Since the first stent-graft component delivered to the aorta aneurysm has three stents at different levels, the graft (the envelope of the first stent-graft component) and stents can be quite large since they can be contracted to a very small diameter for easy delivery of the stent-graft through the ipsilateral arteries by conventional means. If two or more stents were at the same level, it would not be possible to contract the first stent-graft component to the same degree without reducing the size of the distal stents. The first stent-graft component 12 is delivered through the AAA until the proximal end 13A of the first stent-graft component is positioned within the proximal implantation site 30 of the aorta 22. The delivery system slowly releases the first stent-graft component allowing the proximal trunk stent 48 to self-expand to form a union between the inner wall of the undilated portion, i.e., healthy portion, of the aorta 22 and the outer wall of the proximal end of the first stent-graft component 12. The surgeon observes this manipulation by X-ray observation. As the delivery system is withdrawn, leaving the first stent-graft component in the aneurysm 28, the ipsilateral trunk stent 50 expands and then the bell-bottom stent 52 expands to form the bell-bottom. The stents 50 and 52 keep the distal ends of the legs 15A and 15B open for insertion of the second and third stent-graft components 14 and 16. The ipsilateral catheter guide wire 80 utilized to guide the first stent-graft component through the ipsilateral iliac artery 24 and through the aorta aneurysm 28 to the undilated portion of the aorta 22 remains behind as a guide for the insertion, connection, and implantation of the second stent-graft component 14.

Figure 6:
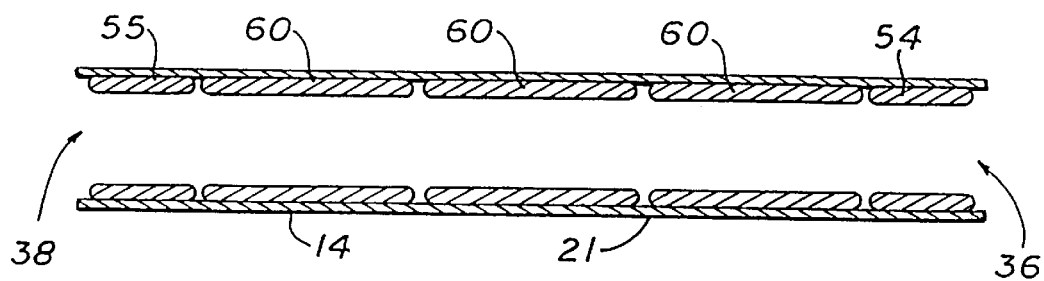
FIG. 6 is a cross-sectional view of the second stent-graft component of the modular stent-graft of FIG. 1.

The delivery system containing the contracted second stent-graft component is guided back to the AAA using the ipsilateral guide wire 80 in the same manner as the guide wire was used to implant the first stent-graft component. As shown in FIG. 6, the second stent-graft component or ipsilateral extension 14 is comprised of a tubular sheath 21 with a plurality of self-expanding stents, the proximal ipsilateral extension stent 54, the distal ipsilateral extension stent 55 and supporting stents 60. The stents are self-expanding and are contracted when inserted into the delivery system. Once the delivery system has correctly positioned the ipsilateral extension in the modular stent-graft and is withdrawn, the stents are sequentially expanded as the delivery system is withdrawn.

Figure 4:
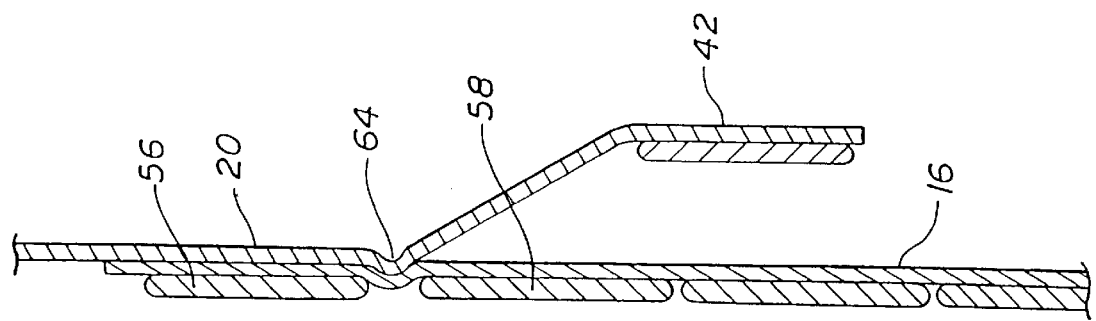
FIG. 4 is a top fragmentary cross-sectional view of the stent-graft of FIG. 1.
Figure 5:
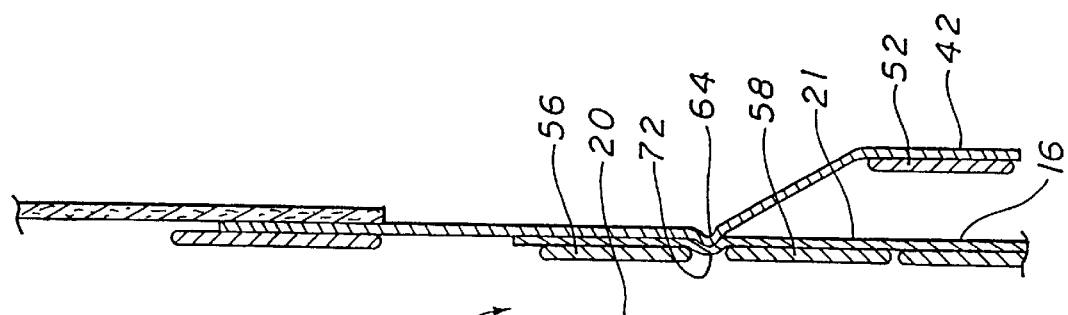
FIG. 5 is an enlarged fragmentary cross-sectional view of the connection between the first stent-graft component and the third stent-graft component of the stent-graft of FIG. 1.

Referring to FIGS. 1 and 4, the proximal end 36 of the ipsilateral extension 14 is inserted into the ipsilateral docking site 18. As the delivery system is withdrawn, the proximal ipsilateral extension stent 54 expands, compressing the tubular sheath 21 between the ipsilateral trunk stent 50 and the proximal ipsilateral extension stent 54. The internal diameter of the ipsilateral trunk stent 50 is greater than the internal diameter opening of the restriction 62, causing a narrow waist 70 to form in the sheath 21 as the proximal ipsilateral extension stent 54 expands. This physically locks or secures the ipsilateral extension 14 to the ipsilateral leg 15A to prevent the ipsilateral extension from slipping out or being pulled out of the first stent-graft component. As the delivery system is fully withdrawn, the distal ipsilateral extension stent 55 expands compressing the sheath 21 against the interior wall of the ipsilateral femoral artery 24 at the ipsilateral distal implantation site 32.

After the surgeon confirms that the ipsilateral extension has been successfully implanted into the ipsilateral iliac artery 24, a contralateral catheter guide wire 82 is then inserted into the AAA through the contralateral iliac artery 26. As mentioned above, the bell-bottom 42 of the first stent-graft component aids the surgeon in snaking the guide wire into the contralateral docking site 20. After the guide wire has been successfully positioned, the delivery system containing the compressed contralateral extension 16, which for all intents and purposes is identical to the ipsilateral extension shown in FIG. 6, is guided along the guide wire 82 so that the proximal end 37 of the contralateral extension is positioned within the contralateral docking site 20. The proximal end of the contralateral extension is positioned in the docking site so that the first proximal contralateral extension stent 56 is positioned above or proximal to the constriction 64 and the second proximal contralateral extension stent 58 is positioned below or distal to the constriction 64. As the delivery system is withdrawn, stents 56 and 58, which are self-expanding, expand forcing the sheath 21 of the contralateral extension to expand out to compress the sheath against the inner walls of the contralateral docking site 20. Since the outer diameter of the expanded stents 56 and 58 are larger than the inner diameter of the constriction 64, a narrow waist 72 is created in the sheath 21. This physically locks or secures the proximal end 37 of the contralateral extension into the docking site 20 of the first stent-graft component. After the surgeon confirms that the proximal end of the contralateral extension has been successfully connected to the contralateral docking site, the surgeon manipulates the distal end 39 of the contralateral extension into the contralateral distal implantation site 34 of the contralateral iliac artery 26. Once this positioning has been completed, the surgeon carefully withdraws the delivery system to permit the distal contralateral extension stent (not shown) to expand and compress the outer wall of the contralateral extension sheath 21 against the inner wall of the contralateral femoral artery. When the surgeon confirms that the contralateral extension has been successfully implanted, the contralateral catheter guide wire is then withdrawn. At this point the modular stent-graft has been successfully implanted to repair the AAA, a repair that not only protects the life of the patient but also enhances the quality of the patient's life, since the aneurysm has been shunted out of the patient's circulatory system and no longer functions as a hydraulic accumulator.

The radioopaque marker 66 in the constriction 64 of the contralateral docking site 20 functions as a marker for the surgeon as he observes the manipulation of the various components during the operation. The marker permits the surgeon to easily locate the positioning of the proximal ipsilateral extension stent and the proximal contralateral extension stent 54, 56 respectively, with respect to the restrictions 62, 64 respectively.

Figure 7:
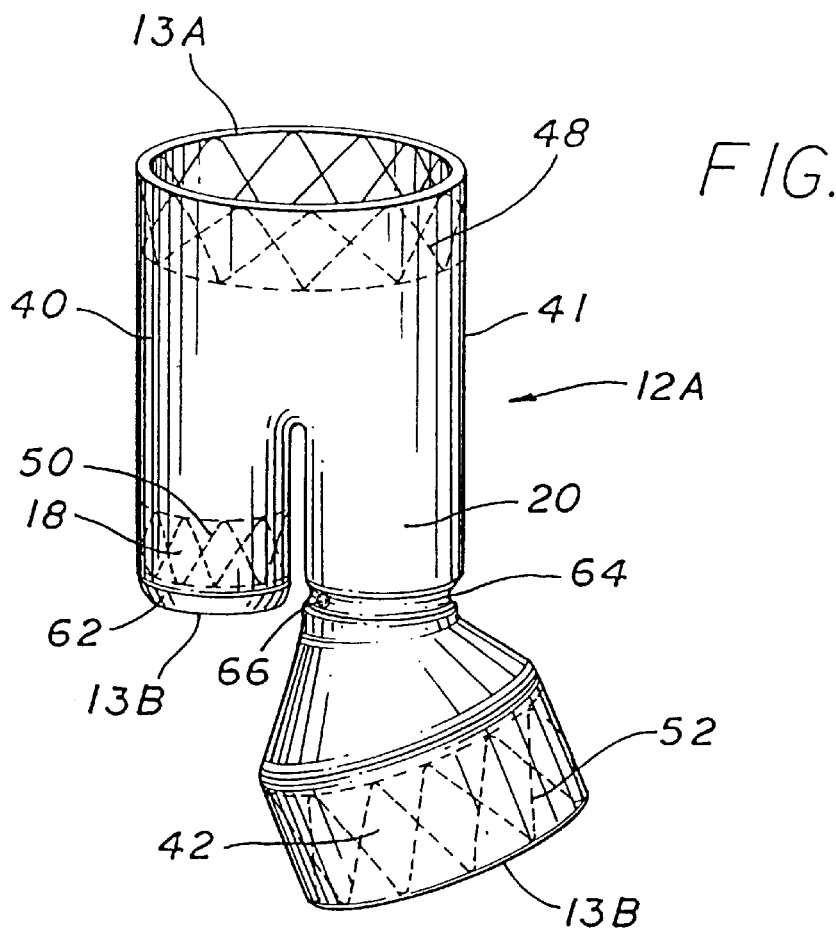
FIG. 7 is a front perspective view of an alternative embodiment of the first stent-graft component of the modular stent-graft of the present invention.

Referring to FIG. 7, an alternative embodiment of the first stent-graft component 12A of the present invention is illustrated wherein the bell-bottom 42 is angled towards the contralateral iliac orifice, making it easier to guide the contralateral catheter guide wire 82 into the contralateral docking site 20, as described above. In all other respects, the first stent-graft component is identical to the stent-graft component 12 described above. The stents 48, 50 and 52 are shown in phantom.

Figure 8:
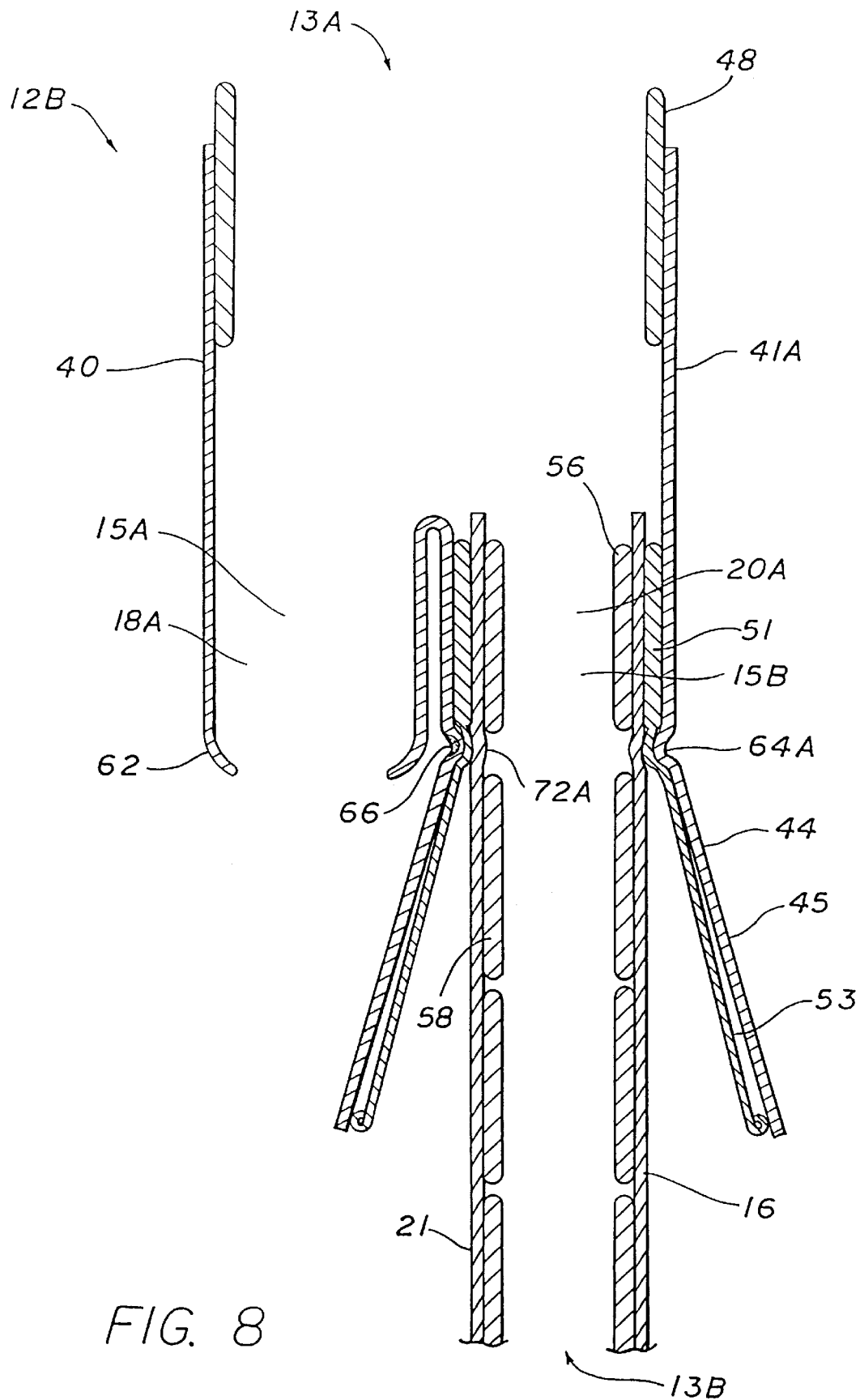
FIG. 8 is a cross-sectional view of a second alternative embodiment of the first stent-graft component of the modular stent-graft of the present invention.

Referring to FIG. 8, a second alterative embodiment of the first stent-graft component 12B of the present invention is illustrated. The ipsilateral docking site 18A is free of an ipsilateral trunk stent which is contained in the first stent-graft component 12 described above. However, the contralateral docking site 20A has a contralateral trunk stent 51 with a series of longitudinal struts 53 extending distally or downwardly from the stents 51 biased to create a conical section with respect to cone 44 of the first stent-graft component. In all other respects, the first stent-graft component 12B is identical to the first stent-graft component 12 described above.

When the alternative embodiment first stent-graft component 12B is utilized to form a modular stent-graft, the proximal end 36 of the ipsilateral extension 14 is positioned slightly above the restriction 62 so that when the proximal ipsilateral extension stent 54 expands, it expands the outer wall of the sheath 21 of the ipsilateral extension against the inner wall of the ipsilateral docking site 18A to seal the ipsilateral extension to the first stent-graft component 12B.

The outer diameter of the proximal ipsilateral extension stent is greater than the inner diameter of the constriction 62 causing the sheath 21 of the ipsilateral extension to form a narrow waist (not shown), thus locking and securing the proximal end of the ipsilateral extension to the ipsilateral docking site 18A to prevent the extension from slipping out or being pulled out of the first stent-graft component 12B. The cone 44 acts in the same manner as the bell-bottom 42 to give the surgeon a greater target area to locate the contralateral catheter guide wire into the contralateral docking site 20A. When the first stent-graft component 12B is in the delivery system, it is compressed and struts 53 are aligned parallel to each other and adjacent to each other. When the delivery system is withdrawn after the first stent-graft component has been implanted into the proximal implantation site 30, the struts 53 expand outwardly to expand the envelope 45 of the cone 44. The struts bow out at the juncture of the constriction 64A so as to help form the narrow waist 72A at the proximal end 37 of the contralateral extension 16. After the contralateral catheter guide wire has been positioned within the contralateral docking site 20A, the proximal end 37 of the contralateral extension 16 is positioned within the docking site. The delivery system is slowly withdrawn, allowing the proximal contralateral extension stent 56 to expand, compressing the sheath 21 of the extension between the inner side of the contralateral trunk stent 51 and the outer side of the first proximal contralateral extension stent 56. The narrow waist 72A formed in the sheath 21 locks or secures the proximal end 37 of the contralateral extension to the contralateral docking site 20A to prevent the extension from slipping out or being pulled out of the docking site.

Figure 9:
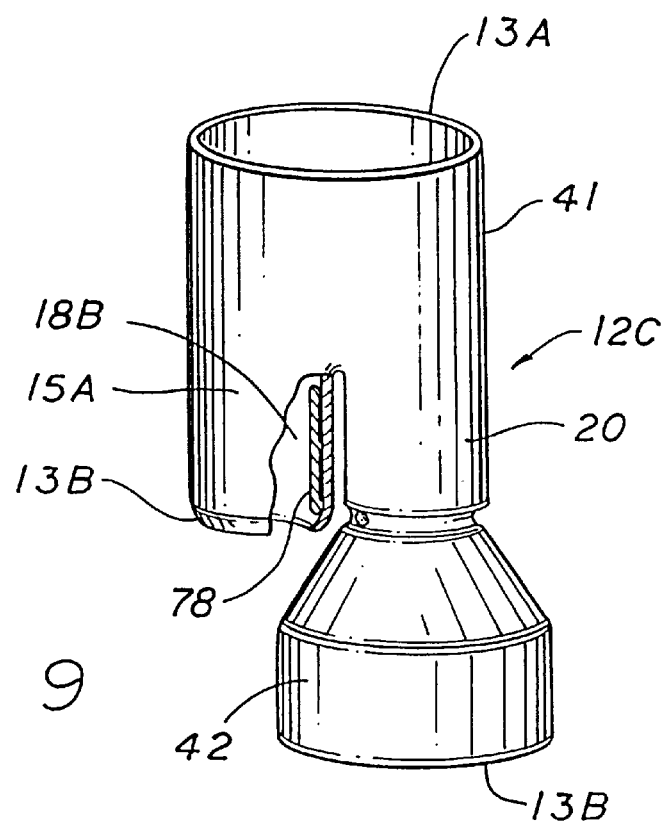
FIG. 9 is a front perspective view of a third alternative embodiment of the first stent-graft component of the modular stent-graft of the present invention.

Referring to FIG. 9, a third alternative stent-graft component 12C is illustrated which is identical to the first stent-graft component 12 described above, with the exception that ipsilateral docking site 18B of this first stent-graft component does not contain an ipsilateral front stent. In contrast, in this first stent-graft component 12C, a flexible bracer 78 is located within the component to prevent longitudinal collapse of the ipsilateral leg 15A during implantation into the proximal implantation site 30. Alternatively, longitudinal collapse of the ipsilateral leg 15A can be prevented in the first stent-graft component 12C described above by attaching ipsilateral leg 15A to contralateral leg 15B by struts attached between the two legs, a membrane attached to the two legs, or by sewing the two legs together (not shown).

I claim:

1. A modular graft assembly, comprising:
   a main graft component including a first end and a second end and having a longitudinal dimension, said second end including a flared configuration;
   at least one auxiliary graft component; and
   a plurality of radial expansion members attached to said main graft component and positioned in a non-overlapping manner along said longitudinal dimension of said main graft component.

2. The modular graft of claim 1, wherein said second end is defined by a first leg and a second leg.

3. The modular graft of claim 2, wherein said second leg has said flared configuration.

4. The modular graft of claim 2, wherein said first leg has a length greater than said second leg.

5. The modular graft of claim 2, said first leg further comprising a terminal end configured with a self-expanding radial expansion members.

6. The modular graft of claim 2, said second leg further comprising a terminal end configured with a self-expanding radial expansion members.

7. The modular graft of claim 2, wherein said modular graft includes a first auxiliary graft component adapted to connect to said first leg.

8. The modular graft of claim 7, said first auxiliary graft component further including radial expansion members configured to urge said first auxiliary graft component into engagement with said first leg of said main graft component.

9. The modular graft of claim 8, wherein said modular graft includes second auxiliary graft component adapted to connect to said second leg.

10. The modular graft of claim 9, said second auxiliary graft component further including radial expansion members configured to urge said second auxiliary graft component into engagement with said second leg of main graft component.

11. The modular graft of claim 2, wherein said flared configuration is characterized by having a first part having an increasing diameter and a second part defining a terminal end of said graft and being continuous with said first part, said second part having a generally constant expanded diameter.

* * * * *

UNITED STATES PATENT AND TRADEMARK OFFICE
CERTIFICATE OF CORRECTION

PATENT NO. : 6,293,969 B1
DATED : September 25, 2001
INVENTOR(S) : Timothy A. M. Chuter It is certified that error appears in the above-identified patent and that said Letters Patent is hereby corrected as shown below:

<u>Column 8,</u>
Line 32, change "2", to read -- 1 --.

Signed and Sealed this

Thirtieth Day of April, 2002

Attest:

Attesting Officer

JAMES E. ROGAN
*Director of the United States Patent and Trademark Office*